US007206416B2

(12) United States Patent
Krause et al.

(10) Patent No.: US 7,206,416 B2
(45) Date of Patent: Apr. 17, 2007

(54) SPEECH-BASED OPTIMIZATION OF DIGITAL HEARING DEVICES

(75) Inventors: Lee S. Krause, Indialantic, FL (US); Rahul Shrivastav, Gainesville, FL (US); Alice E. Holmes, Gainesville, FL (US); Purvis Bedenbaugh, Gainesville, FL (US)

(73) Assignees: University of Florida Research Foundation, Inc., Gainesville, FL (US); Audigence, Inc., Indialantic, FL (US)

( * ) Notice: Subject to any disclaimer, the term of this patent is extended or adjusted under 35 U.S.C. 154(b) by 146 days.

(21) Appl. No.: 10/872,313

(22) Filed: Jun. 18, 2004

(65) Prior Publication Data

US 2005/0027537 A1 Feb. 3, 2005

Related U.S. Application Data

(60) Provisional application No. 60/492,103, filed on Aug. 1, 2003.

(51) Int. Cl.
*H04R 29/00* (2006.01)
*A61B 5/00* (2006.01)

(52) U.S. Cl. ......................... 381/60; 600/559; 704/271

(58) Field of Classification Search .................. 381/60, 381/312, 315, 56, 58; 600/559; 704/271; 73/585
See application file for complete search history.

(56) References Cited

U.S. PATENT DOCUMENTS 4,049,930 A * 9/1977 Fletcher et al. ............... 381/60
4,327,252 A * 4/1982 Tomatis ....................... 381/58
5,008,942 A * 4/1991 Kikuchi ....................... 704/270
6,035,046 A * 3/2000 Cheng et al. ................. 381/59
6,036,496 A * 3/2000 Miller et al. ................ 434/156
6,118,877 A * 9/2000 Lindemann et al. .......... 381/60
6,446,038 B1 * 9/2002 Bayya et al. ............... 704/232
6,684,063 B2 1/2004 Berger et al.
6,763,329 B2 7/2004 Brandel et al.
6,823,171 B1 11/2004 Kaario
6,823,312 B2 11/2004 Mittal et al.
6,913,578 B2 7/2005 Hou
6,914,996 B2 7/2005 Takeda
2002/0120440 A1 * 8/2002 Zhang ........................ 704/215
2003/0007647 A1 * 1/2003 Nielsen et al. ................ 381/60

FOREIGN PATENT DOCUMENTS

| | | |
|---|---|---|
| EP | 1519625 | 3/2005 |
| JP | 2002-291062 | 10/2002 |
| WO | WO 98/44762 | 10/1998 |
| WO | WO 2005/062766 | 7/2005 |

OTHER PUBLICATIONS

Runkle, P., et al., "Active Sensory Tuning for Immersive Spatialized Audio", ICAD, (2000).

* cited by examiner

*Primary Examiner*—Xu Mei
(74) *Attorney, Agent, or Firm*—Akerman Senterfitt

(57) ABSTRACT

A method of tuning a digital hearing device can include playing portions of test audio, wherein each portion of test audio represents one or more distinctive features of speech. The method also can include receiving user responses to played portions of test audio heard through the digital hearing device and comparing the user responses with the portions of test audio. An operational parameter of the digital hearing device can be adjusted according to the comparing step, wherein the operational parameter is associated with one or more of the distinctive features of speech.

33 Claims, 3 Drawing Sheets

300

| Parameter | Default | Options |
|---|---|---|
| Strategy | ACE | Ace, CIS, SPEAK |
| Stimulation Rate | 750 Hz | 250 – 2400 Hz |
| Pulse width | 25μs | 25 – 400μs |
| Number of Channels | 20 | < 22 |
| Number of maxima | 8 | < 12 |
| Frequency allocation | Log-linear from 250-10000 Hz | Multiple options |
| Gain | Flat | Multiple options |
| Global threshold and comfort modifiers | None | Increments of 1 - 30% |
| Q-Value | 20 | < 30 |
| Base Level | 4 | 0-6 |
| Jitter | 0% | 20% |

FIG. 3A

305

CI Mapping Strategy Parameters

In general the following principals apply for the CI Device Speech Processing strategies:

- Spectral resolution (SPEAK)
    - Site of stimulation: channel selection
    - Large number of channels desirable
- Temporal resolution (CIS)
    - Amplitude pattern of stimulation at a site
    - High pulse rate on each channel desirable
- The ACE strategy is a combination of both spectral and temporal resolution Parameters that must be chosen prior to measurements of Thresholds and Comfort Values:

1. Stimulation Rate ***
    a. For CIS: rate X number of Channels < 14,400 Hz
    b. For ACE and SPEAK: Rate X number of Maxima <14,400 Hz
2. Pulse width (Default is 25 μs; range is from 25 - 150 μs)

*** for higher stimulation rates the Ts and Cs measured can be used for either an ACE or CIS map as long as the total stimulation rate does not exceed 14,400 Hz Parameters that can be changed once the Threshold and Comfort Values have been obtained:

1) Number of Channels (CIS) or number of maxima (SPEAK or ACE) as long as total stimulation rate does not exceed 14,400 Hz
2) Deactivation of selected channels
3) Frequency Allocation
4) Gain – either globally or for individual channels
5) Global T and C modifiers
6) Q-Value – global modifier that changes the slope digital input level to the stimulus level output – amplitude curve
7) Base Level – minimum input level that produces stimulation
    a. Decreasing: softer sounds are audible [increases the Input Dynamic Range (IDR) of the processor]
    b. Increasing: softer sounds are not processed
8) Jitter: % of random variation to pu lse rate
9) Channel ordering – in very rare cases the cochlea does not follow the normal tonotopic organization of the normal auditory system

FIG. 3B

SPEECH-BASED OPTIMIZATION OF DIGITAL HEARING DEVICES

CROSS-REFERENCE TO RELATED APPLICATIONS

This application claims the benefit of U.S. Provisional Application No. 60/492,103, filed in the United States Patent and Trademark Office on Aug. 1, 2003, the entirety of which is incorporated herein by reference.

BACKGROUND

1. Field of the Invention

This invention relates to the field of digital hearing enhancement systems.

2. Description of the Related Art

Multi-channel Cochlear Implant (CI) systems consist of an external headset with a microphone and transmitter, a body-worn or ear-level speech processor with a battery supply, and an internal receiver and electrode array. The microphone detects sound information and sends it to the speech processor which encodes the sound information into a digital signal. This information then is sent to the headset so that the transmitter can send the electrical signal through the skin via radio frequency waves to the internal receiver located in the mastoid bone of an implant recipient.

The receiver sends the electrical impulses to the electrodes implanted in the cochlea, thus stimulating the auditory nerve such that the listener receives sound sensations. Multi-channel CI systems utilize a plurality of sensors or electrodes. Each sensor is associated with a corresponding channel which carries signals of a particular frequency range. Accordingly, the sensitivity or amount of gain perceived by a recipient can be altered for each channel independently of the others.

Over recent years, CI systems have made significant strides in improving the quality of life for profoundly hard of hearing individuals. CI systems have progressed from providing a minimal level of tonal response to allowing individuals having the implant to recognize upwards of 80 percent of words in test situations. Much of this improvement has been based upon improvements in speech coding techniques. For example, the introduction of Advanced Combination Encoders (ACE), Continuous Interleaved Sampling (CIS) and HiResolution, have contributed to improved performance for CI systems, as well as other digital hearing enhancement systems which incorporate multi-channel and/or speech processing techniques.

Once a CI system is implanted in a user, or another type-of digital hearing enhancement mechanism is worn by a user, a suitable speech coding strategy and mapping strategy must be selected to enhance the performance of the CI system for day-to-day operation. Mapping strategy refers to the adjustment of parameters corresponding to one or more independent channels of a multi-channel CI system or other hearing enhancement system. Selection of each of these strategies typically occurs over an introductory period of approximately 6 or 7 weeks during which the hearing enhancement system is tuned. During this tuning period, users of such systems are asked to provide feedback on how they feel the device is performing. The tuning process, however, is not a user-specific process. Rather, the tuning process is geared to the average user.

More particularly, to create a mapping for a speech processor, an audiologist first determines the electrical dynamic range for each electrode or sensor used. The programming system delivers an electrical current through the CI system to each electrode in order to obtain the electrical threshold (T-level) and comfort or max level (C-level) measures defined by the device manufacturers. T-level, or minimum stimulation level, is the softest electrical current capable of producing an auditory sensation in the user 100 percent of the time. The C-level is the loudest level of signal to which a user can listen comfortably for a long period of time.

The speech processor then is programmed, or "mapped," using one of several encoding strategies so that the electrical current delivered to the implant will be within this measured dynamic range, between the T and C-levels. After T and C-levels are established and the mapping is created, the microphone is activated so that the patient is able to hear speech and sounds in the environment. From that point on, the tuning process continues as a traditional hearing test. Hearing enhancement device users are asked to listen to tones of differing frequencies and volumes. The gain of each channel further can be altered within the established threshold ranges such that the patient is able to hear various tones of differing volumes and frequencies reasonably well. Accordingly, current tuning practice focuses on allowing a user to become acclimated to the signal generated by the hearing device.

The above-mentioned tuning technique has been developed to meet the needs of the average user. This approach has gained favor because the amount of time and the number of potential variables involved in designing optimal maps for individual users would be too daunting a task. For example, additional complications to the tuning process exist when users attempt to add subjective input to the tuning of the hearing enhancement system. Using subjective input from a user can add greater complexity to the tuning process as each change in the mapping of a hearing enhancement system requires the user to adjust to a new signal. Accordingly, after a mapping change, users may believe that their ability to hear has been enhanced, while in actuality, the users have not adjusted to the new mapping. As users adjust to new mappings, the users' hearing may in fact have been degraded.

What is needed is a technique of tuning hearing enhancement systems, including both CI systems and digital hearing aids, that bypasses user subjectivity, while still allowing hearing enhancement systems to be tuned on an individual basis. Further, such a technique should be time efficient.

SUMMARY OF THE INVENTION

In one embodiment, the present invention provides a solution for tuning hearing enhancement systems. The inventive arrangements disclosed herein can be used with a variety of digital hearing enhancement systems including, but not limited to, digital hearing aids and cochlear implant systems (hereafter collectively "hearing devices"). In accordance with the present invention, rather than using conventional hearing tests where only tones are used for purposes of testing a hearing device, speech perceptual tests can be used.

More particularly, speech perceptual tests wherein various words and/or syllables of the test are representative of distinctive language and/or speech features can be correlated with adjustable parameters of a hearing device. By detecting words and/or syllables that are misrecognized by a user, the hearing device can be tuned to achieve improved performance over conventional methods of tuning hearing devices.

Still, in other embodiments, the present invention provides a solution for characterizing various communications channels and adjusting those channels to overcome distortions and/or other deficiencies.

One aspect of the present invention can include a method of tuning a digital hearing device. The method can include playing portions of test audio, wherein each portion of test audio represents one or more distinctive features of speech, receiving user responses to played portions of test audio heard through the digital hearing device, and comparing the user responses with the portions of test audio. An operational parameter of the digital hearing device can be adjusted according to the comparing step, wherein the operational parameter is associated with one or more of the distinctive features of speech.

In another embodiment, the method can include, prior to the adjusting step, associating one or more of the distinctive features of the portions of test audio with the operational parameter of the digital hearing device. Each distinctive feature of speech can be associated with at least one frequency or temporal characteristic. Accordingly, the operational parameter can control processing of frequency and/or temporal characteristics associated with at least one of the distinctive features.

The method further can include determining that at least a portion of the digital hearing device is located in a sub-optimal location according to the comparing step. The steps described herein also can be performed for at least one different language as well as for a plurality of different users of similar hearing devices.

Another aspect of the present invention can include a method of evaluating a communication channel. The method can include playing, over the communication channel, portions of test audio, wherein each portion of test audio represents one or more distinctive features of speech. The method can include receiving user responses to played portions of test audio, comparing the user responses with the portions of test audio, and associating distinctive features of the portions of test audio with operational parameters of the communication channel.

In another embodiment, the method can include adjusting at least one of the operational parameters of the communication channel according to the comparing and associating steps. Notably, the communication channel can include an acoustic environment formed by an architectural structure, an underwater acoustic environment, or the communication channel can mimic aviation effects on speech and hearing. For example, the communication channel can mimic effects such as G-force, masks, and the Lombard effect on hearing. The steps disclosed herein also can be performed in cases where the user exhibits signs of stress or fatigue.

Other embodiments of the present invention can include a machine readable storage programmed to cause a machine to perform the steps disclosed herein as well as a system having means for performing the various steps described herein.

BRIEF DESCRIPTION OF THE DRAWINGS

There are shown in the drawings, embodiments which are presently preferred, it being understood, however, that the invention is not limited to the precise arrangements and instrumentalities shown.

FIGS. 3A and 3B are tables illustrating exemplary operational parameters of one variety of hearing enhancement system, such as a Cochlear Implant, that can be modified using suitable control software.

DETAILED DESCRIPTION OF THE INVENTION

Figure 1:
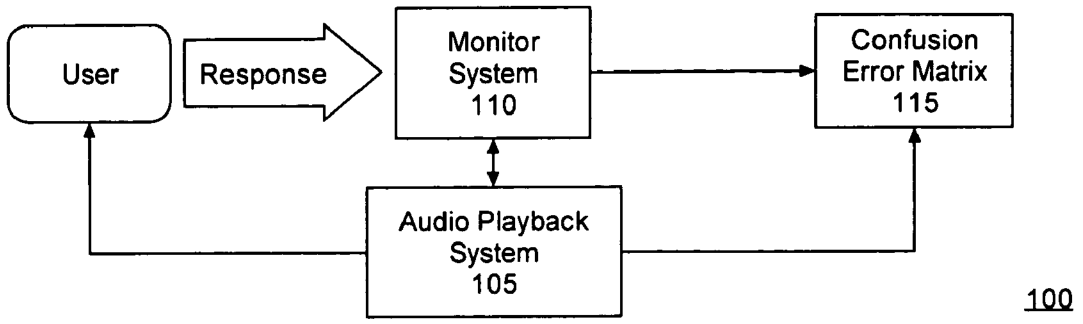
FIG. 1 is a schematic diagram illustrating an exemplary system for determining relationships between distinctive features of speech and adjustable parameters of a hearing enhancement system in accordance with the inventive arrangements disclosed herein.

FIG. 1 is a schematic diagram illustrating an exemplary system 100 for determining relationships between distinctive speech and/or language features and adjustable parameters of a hearing enhancement system (hearing device) in accordance with the inventive arrangements disclosed herein. As noted, hearing devices can include any of a variety of digital hearing enhancement systems such as cochlear implant systems, digital hearing aids, or any other such device having digital processing and/or speech processing capabilities. The system 100 can include an audio playback system (playback system) 105, a monitor 110, and a confusion error matrix (CEM) 115.

The playback system 105 can audibly play recorded words and/or syllables to a user having a hearing device to be tuned. The playback system 105 can be any of a variety of analog and/or digital sound playback systems. According to one embodiment of the present invention, the playback system 105 can be a computer system having digitized audio stored therein. In another example, the playback system 105 can include a text-to-speech (TTS) system capable of generating synthetic speech from input or stored text.

While the playback system 105 can simply play recorded and/or generated audio aloud to a user, it should be appreciated that in some cases the playback system 105 can be communicatively linked with the hearing device under test. For example, in the case of selected digital hearing aids and/or cochlear implant systems, an A/C input jack can be included in the hearing device that allows the playback system 105 to be connected to the hearing device to play audio directly through the A/C input jack without having to generate sound via acoustic transducers.

The playback system 105 can be configured to play any of a variety of different test words and/or syllables to the user (test audio). Accordingly, the playback system 105 can include or play commonly accepted test audio. For example, according to one embodiment of the present invention, the well known Iowa Test Battery, as disclosed by Tyler et al. (1986), of consonant vowel consonant nonsense words can be used. As noted, depending upon the playback system 105, a media such as a tape or compact disc can be played, the test battery can be loaded into a computer system for playback, or the playback system 105 can generate synthetic speech mimicking a test battery.

Regardless of the particular set or listing of words and/or syllables used, each of the words and/or syllables can represent a particular set of one or more distinctive features of speech. Two distinctive feature sets have been proposed. The first set of features has been proposed by Chompsky and Halle (1968). This set of features is based upon the articulatory positions underlying the production of speech sounds. Another set of features, proposed by Jakobson, Fant, and Halle (1963), is based upon the acoustic properties of various speech sounds. These properties describe a small set of contrastive acoustic properties that are perceptually relevant for the discrimination of pairs of speech sounds. An exemplary listing of such properties can include, but is not limited to, compact vs. diffuse, grave vs. acute, tense vs. lax, and strident vs. mellow.

It should be appreciated that any of a variety of different features of speech can be used within the context of the present invention. Any feature set that can be correlated to test words and/or syllables can be used. As such, the invention is not limited to the use of a particular set of speech features and further can utilize a conglomeration of one or more feature sets.

The monitor system 110 can be a human being who records the various test words/syllables provided to the user and the user responses. In another embodiment, the monitor system 110 can be a speech recognition system configured to speech recognize, or convert to text, user responses. For example, after hearing a word and/or syllable, the user can repeat the perceived test audio aloud.

In yet another embodiment, the monitor system 110 can include a visual interface through which the user can interact. The monitor system can include a display upon which different selections are shown. Thus, the playback of particular test words or syllables can be coordinated and/or synchronized with the display of possible answer selections that can be chosen by the user. For example, if the playback system 105 played the word "Sam", possible selections could include the correct choice "Sam" and one or more incorrect choices such as "sham". The user chooses the selection corresponding to the user's understanding or ability to perceive the test audio.

In any case, the monitor system 110 can note the user response and store the result in the CEM 115. The CEM 115 is a log of which words and/or syllables were played to the user and the user responses. The CEM 115 can store both textual representations of test audio and user responses and/or the audio itself, for example as recorded through a computer system or other audio recording system. As shown, the audio playback system 105 can be communicatively linked to the CEM 115 so that audio data played to the user can be recorded within the CEM 115.

While the various components of system 100 have been depicted as being separate or distinct components, it should be appreciated that various components can be combined or implemented using one or more individual machines or systems. For example, if a computer system is utilized as the playback system 105, the same computer system also can store the CEM 115. Similarly, if a speech recognition system is used, the computer system can include suitable audio circuitry and execute the appropriate speech recognition software.

Depending upon whether the monitor system 115 is a human being or a machine, the system 100, for example the computer, can be configured to automatically populate the confusion error matrix 115 as the testing proceeds. In that case, the computer system further can coordinate the operation of the monitor system 110, the playback system 105, and access to the CEM 115. Alternatively, a human monitor 110 can enter testing information into the CEM 115 manually.

Figure 2:
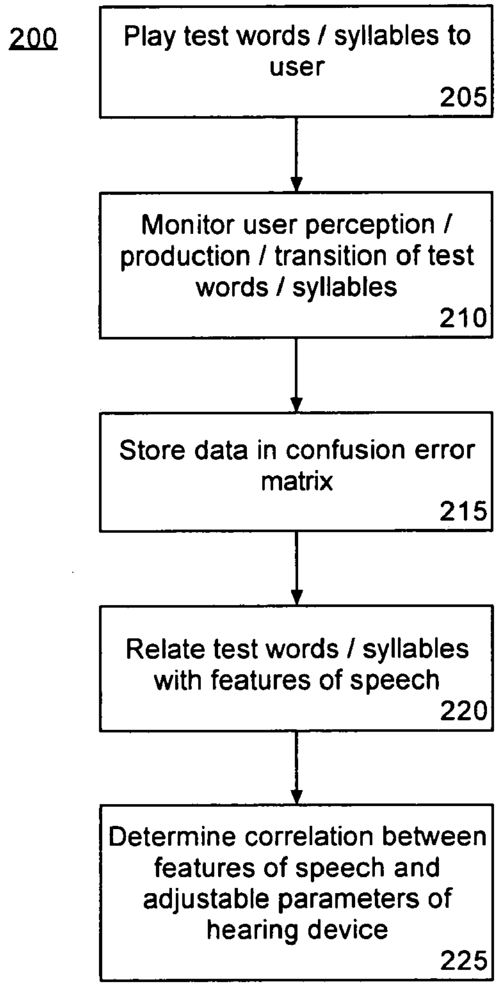
FIG. 2 is a flow chart illustrating a method of determining relationships between distinctive features of speech and adjustable parameters of hearing enhancement systems in accordance with the inventive arrangements disclosed herein.

FIG. 2 is a flow chart illustrating a method 200 of determining relationships between features of speech and adjustable parameters of hearing devices in accordance with the inventive arrangements disclosed herein. The method 200 can begin in a state where a hearing device worn by a user is to be tuned. In accordance with one aspect of the present invention, the user has already undergone an adjustment period of using the hearing device. For example, as the method 200 is directed to determining relationships between distinctive features of speech and parameters of a hearing device, it may be desirable to test a user who has already had ample time to physically adjust to wearing a hearing device.

The method 200 can begin in step 205 where a set of test words and/or syllables can be played to the user. In step 210, the user's understanding of the test audio can be monitored. That is, the user's perception of what is heard, production of what was heard, and transition can be monitored. For example, in one aspect of the present invention, the user can repeat any perceived audio aloud. As noted, the user responses can be automatically recognized by a speech recognition system or can be noted by a human monitor. In another aspect, the user can select an option from a visual interface indicating what the user perceived as the test audio.

In step 215, the test data can be recorded into the confusion error matrix. For example, the word played to the user can be stored in the CEM, whether as text, audio, and/or both. Similarly, the user responses can be stored as audio, textual representations of audio or speech recognized text, and/or both. Accordingly, the CEM can maintain a log of test words/syllables and matching user responses. It should be appreciated by those skilled in the art that the steps 205, 210 and 215 can be repeated for individual users such that portions of test audio can be played sequentially to a user until completion of a test.

After obtaining a suitable amount of test data, analysis can begin. In step 220, each error on the CEM can be analyzed in terms of a set of distinctive features represented by the test word or syllable. The various test words and/or syllables can be related or associated with the features of speech for which each such word and/or syllable is to test. Accordingly, a determination can be made as to whether the user was able to accurately perceive each of the distinctive features as indicated by the user's response. The present invention contemplates detecting both the user's perception of test audio as well as the user's speech production, for example in the case where the user responds by speaking back the test audio that is perceived. Mispronunciations by the user can serve as an indicator that one or more of the distinctive features represented by the mispronounced word or syllable are not being perceived correctly despite the use of the hearing device. Thus, either one or both methods can be used to determine the distinctive features that are perceived correctly and those that are not.

In step 225, correlations between features of speech and adjustable parameters of a hearing device can be determined. For example, such correlations can be determined through an empirical, iterative process where different parameters of hearing devices are altered in serial fashion to determine whether any improvements in the user's perception and/or production result. Accordingly, strategies for altering parameters of a hearing device can be formulated based upon the CEM determined from the user's test session or during the test session.

In illustration, studies have shown that with respect to the distinctive features referred to as grave sounds, such sounds are characterized by a predominance of energy in the low frequency range of speech. Acute sounds, on the other hand, are characterized by energy in the high frequency range of speech. Accordingly, test words and/or syllables representing grave or acute sounds can be labeled as such. When a word exhibiting a grave or acute feature is misrecognized by a user, the parameters of the hearing device that affect the capability of the hearing device to accurately portray high or low frequencies of speech, as the case may be, can be altered. Thus, such parameters can be associated with the misrecognition of acute and/or grave features by a user. Similarly, interrupted sounds are those that have a sudden onset, whereas continuant sounds have a more gradual onset. Users who are not able to adequately discriminate this contrast may benefit from adjustments to device settings that enhance such a contrast.

According to one embodiment of the present invention, Modeling Field Theory (MFT) can be used to determine relationships between operational parameters of hearing devices and the recognition and/or production of distinctive features. MFT has the ability to handle combinatorial complexity issues that exist in the hearing device domain. MFT, as advanced by Perlovsky, combines a priori knowledge representation with leaning and fuzzy logic techniques to represent intellect. The mind operates through a combination of complicated a priori knowledge or experience with learning. The optimization of the CI sensor map strategy mimics this type of behavior since the tuning parameters may have different effects on different users.

Still, other computational methods can be used including, but not limited to, genetic algorithms, neural networks, fuzzy logic, and the like. Accordingly, the inventive arrangements disclosed herein are not limited to the use of a particular technique for formulating strategies for adjusting operational parameters of hearing devices based upon speech, or for determining relationships between operational parameters of hearing devices and recognition and/or perception of features of speech.

FIG. 3A is a table 300 listing examples of common operational parameters of hearing devices that can be modified through the use of a suitable control system, such as a computer or information processing system having appropriate software for programming such devices. FIG. 3B is a table 305 illustrating further operational parameters of hearing devices that can be modified using an appropriate control system. Accordingly, through an iterative testing process where a sampling of individuals are tested, relationships between test words, and therefore associated features of speech, and operational parameters of hearing devices can be established. By recognizing such relationships, strategies for improving the performance of a hearing device can be formulated based upon the CEM of a user undergoing testing. As such, hearing devices can be tuned based upon speech rather than tones.

Figure 4:
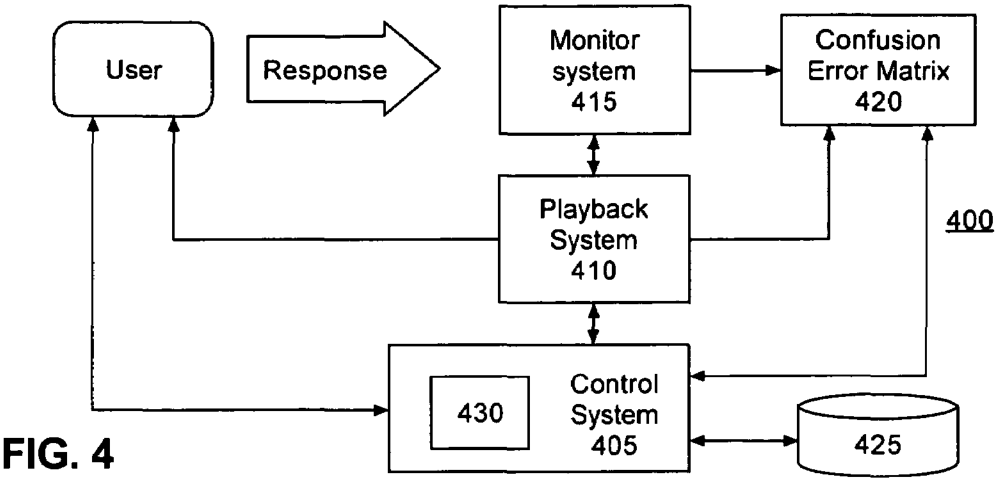
FIG. 4 is a schematic diagram illustrating an exemplary system for determining a mapping for a hearing enhancement system in accordance with the inventive arrangements disclosed herein.

FIG. 4 is a schematic diagram illustrating an exemplary system 400 for determining a mapping for a hearing device in accordance with the inventive arrangements disclosed herein. As shown, the system 400 can include a control system 405, a playback system 410, and a monitor system 415. The system 400 further can include a CEM 420 and a feature to map parameter knowledge base (knowledge base) 425.

The playback system 410 can be similar to the playback system as described with reference to FIG. 1. The playback system 410 can play audio renditions of test words and/or syllables and can be directly connected to the user's hearing device. Still, the playback system 410 can play words and/or syllables aloud without a direct connection to the hearing device.

The monitor system 415 also can be similar to the monitor system of FIG. 1. Notably, the playback system 410 and the monitor system 415 can be communicatively linked thereby facilitating operation in a coordinated and/or synchronized manner. For example, in one embodiment, the playback system 410 can present a next stimulus only after the response to the previous stimulus has been recorded. The monitor system 415 can include a visual interface allowing users to select visual responses corresponding to the played test audio, for example various correct and incorrect textual representations of the played test audio. The monitor system 415 also can be a speech recognition system or a human monitor.

The CEM 420 can store a listing of played audio along with user responses to each test word and/or syllable. The knowledge base 425 can include one or more strategies for improving the performance of a hearing device as determined through iteration of the method of FIG. 2. The knowledge base 425 can be cross-referenced with the CEM 420, allowing a mapping for the user's hearing device to be developed in accordance with the application of one or more strategies as determined from the CEM 420 during testing. The strategies can specify which operational parameters of the hearing device are to be modified based upon errors noted in the CEM 420 determined in the user's test session.

The control system 405 can be a computer and/or information processing system which can coordinate the operation of the components of system 400. The control system 405 can access the CEM 420 being developed in a test session to begin developing an optimized mapping for the hearing device under test. More particularly, based upon the user's responses to test audio, the control system 405 can determine proper parameter settings for the user's hearing device.

In addition to initiating and controlling the operation of each of the components in the system 400, the control system 405 further can be communicatively linked with the hearing device worn by the user. Accordingly, the control system 405 can provide an interface through which modifications to the user's hearing device can be implemented, either under the control of test personnel such as an audiologist, or automatically under programmatic control based upon the user's resulting CEM 420. For example, the mapping developed by the control system 405 can be loaded in to the hearing device under test.

While the system 400 can be implemented in any of a variety of different configurations, including the use of individual components for one or more of the control system 405, the playback system 410, the monitor system 415, the CEM 420, and/or the knowledge base 425, according to another embodiment of the present invention, the components can be included in one or more computer systems having appropriate operational software.

Figure 5:
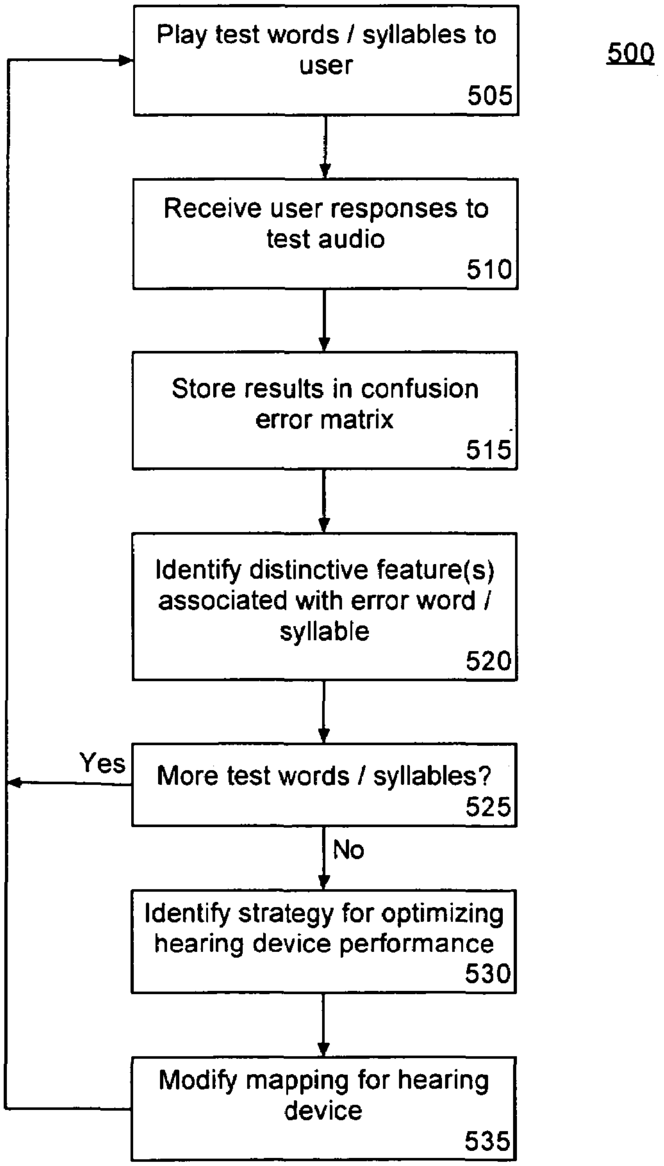
FIG. 5 is a flow chart illustrating a method of determining a mapping for a hearing enhancement system in accordance with the inventive arrangements disclosed herein.

FIG. 5 is a flow chart illustrating a method 500 of determining a mapping for a hearing device in accordance with the inventive arrangements disclosed herein. The method 500 can begin in a state where a user, wearing a hearing device, is undergoing testing to properly configure the hearing device. Accordingly, in step 505, the control system can instruct the playback system to begin playing test audio in a sequential manner.

As noted, the test audio can include, but is not limited to, words and/or syllables including nonsense words and/or syllables. Thus, a single word and/or syllable can be played. As portions of test audio are played, entries corresponding to the test audio can be made in the CEM indicating which word or syllable was played. Alternatively, if the ordering of words and/or syllables is predetermined, the CEM need not include a listing of the words and/or syllables used as the user's responses can be correlated with the predetermined listing of test audio.

In step 510, a user response can be received by the monitor system. The user response can indicate the user's perception of what was heard. If the monitor system is visual, as each word and/or syllable is played, possible solutions can be displayed upon a display screen. For example, if the playback system played the word "Sam", possible selections could include the correct choice "Sam" and an incorrect choice of "sham". The user chooses the selection corresponding to the user's understanding or ability to perceive the test audio.

In another embodiment, the user could be asked to repeat the test audio. In that case the monitor system can be implemented as a speech recognition system for recognizing the user's responses. Still, as noted, the monitor can be a human being annotating each user's response to the ordered set of test words and/or syllables. In any event, it should be appreciated that depending upon the particular configuration of the system used, a completely automated process is contemplated.

In step 515, the user's response can be stored in the CEM. The user's response can be matched to the test audio that was played to illicit the user response. It should be appreciated that, if so configured, the CEM can include text representations of test audio and user responses, recorded audio representations of test audio and user responses, or any combination thereof.

In step 520, the distinctive feature or features represented by the portion of test audio can be identified. For example, if the test word exhibits grave sound features, the word can be annotated as such. In step 525, a determination can be made as to whether additional test words and/or syllables remain to be played. If so, the method can loop back to step 505 to repeat as necessary. If not, the method can continue to step 530. It should be appreciated that samples can be collected and a batch type of analysis can be run at the completion of the testing rather than as the testing is performed.

In step 530, based upon the knowledge base, a strategy for adjusting the hearing device to improve the performance of the hearing device with respect to the distinctive feature(s) can be identified. As noted, the strategy can specify one or more operational parameters of the hearing device to be changed to correct for the perceived hearing deficiency. Notably, the implementation of strategies can be limited to only those cases where the user misrecognizes a test word or syllable.

For example, if test words having grave sound features were misrecognized, a strategy directed at correcting such misperceptions can be identified. As grave sound features are characterized by a predominance of energy in the low frequency range of speech, the strategy implemented can include adjusting parameters of the hearing device that affect the way in which low frequencies are processed. For instance, the strategy can specify that the mapping should be updated so that the gain of a channel responsible for low frequencies is increased. In another embodiment, the frequency ranges of each channel of the hearing device can be varied.

It should be appreciated that the various strategies can be formulated to interact with one another. That is, the strategies can be implemented based upon an entire history of recognized and misrecognized test audio rather than only a single test word or syllable. As the nature of a user's hearing is non-linear, the strategies further can be tailored to adjust more than a single parameter as well as offset the adjustment of one parameter with the adjusting (i.e. raising or lowering) of another. In step 535, a mapping being developed for the hearing device under test can be modified. In particular, a mapping, whether a new mapping or an existing mapping, for the hearing device can be updated according to the specified strategy.

It should be appreciated, however, that the method 500 can be repeated as necessary to further develop a mapping for the hearing device. According to one aspect of the present invention, particular test words and/or syllables can be replayed, rather than the entire test set, depending upon which strategies are initiated to further fine tune the mapping. Once the mapping is developed, the mapping can be loaded into the hearing device.

Those skilled in the art will recognize that the inventive arrangements disclosed herein can be applied to a variety of different languages. For example, to account for the importance of various distinctive features from language to language, each strategy can include one or more weighted parameters specifying the degree to which each hearing device parameter is to be modified for a particular language. The strategies of such a multi-lingual test system further can specify subsets of one or more hearing device parameters that may be adjusted for one language but not for another language. Accordingly, when a test system is started, the system can be configured to operate or conduct tests for an operator specified language. Thus, test audio also can be stored and played for any of a variety of different languages.

The present invention also can be used to overcome hearing device performance issues caused by the placement of the device within a user. For example, the placement of a cochlear implant within a user can vary from user to user. The tuning method described herein can improve performance caused, at least in part, by the particular placement of cochlear implant.

Still, the present invention can be used to adjust, optimize, compensate, or model communication channels, whether an entire communication system, particular equipment, etc. Thus, by determining which distinctive features of speech are misperceived or are difficult to identify after the test audio has been played through the channel, the communication channel can be modeled. The distinctive features of speech can be correlated to various parameters and/or settings of the communication channel for purposes of adjusting or tuning the channel for increased clarity.

For example, the present invention can be used to characterize the acoustic environment resulting from a structure such as a building or other architectural work. That is, the effects of the acoustic and/or physical environment in which the speaker and/or listener is located can be included as part of the communication system being modeled. In another example, the present invention can be used to characterize and/or compensate for an underwater acoustic environment. In yet another example, the present invention can be used to model and/or adjust a communication channel or system to accommodate for aviation effects such as effects on hearing resulting from increased G-forces, the wearing of a mask by a listener and/or speaker, or the Lombard effect. The present invention also can be used to characterize and compensate for changes in a user's hearing or speech as a result of stress, fatigue, or the user being engaged in deception.

The present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention. Each of the references cited herein is fully incorporated by reference.

What is claimed is:

1. A method of tuning a digital hearing device comprising:

playing portions of test audio, wherein each portion of test audio comprises a test word or syllable that is correlated with one or more distinctive features of speech;

for each of the portions of test audio when heard by a user through the digital hearing device, receiving a corresponding user response prior to a subsequent portion of test audio being played;

recording each user response and generating a confusion error matrix based upon the recorded user responses;

analyzing the confusion error matrix to determine the user's ability to accurately perceive distinctive features correlated with a test word or syllable presented; and adjusting at least one operational parameter of the digital hearing device according to said analyzing step, wherein the at least one operational parameter is associated with the one or more distinctive features of speech.

2. The method of claim 1, further comprising, prior to said adjusting step, associating the one or more distinctive features of the portions of test audio with the operational parameter of the digital hearing device.

3. The method of claim 1, wherein each distinctive feature of speech is associated with at least one frequency characteristic and the operational parameter controls processing of frequency characteristics associated with at least one of the distinctive features.

4. The method of claim 1, wherein each distinctive feature of speech is associated with at least one temporal characteristic and the operational parameter controls processing of temporal characteristics associated with at least one of the distinctive features.

5. The method of claim 1, further comprising determining that at least a portion of the digital hearing device is sub-optimally configured for a particular user based upon said analyzing step.

6. The method of claim 1, further comprising performing each said step of claim 1 for at least one different language.

7. The method of claim 1, further comprising performing each said step of claim 1 for a plurality of different users of similar hearing devices.

8. The method of claim 1, wherein each distinctive feature of speech is associated with at least one relative intensity characteristic and the operational parameter controls processing of relative intensity characteristics associated with at least one of the distinctive features.

9. A method of evaluating a communication channel comprising:

playing, over the communication channel, portions of test audio, wherein each portion of test audio comprises a test word or syllable that is correlated with one or more distinctive features of speech;

for each portion of test audio when heard by a user over the communication channel, receiving a corresponding user response prior to a subsequent portion of test audio being played;

recording each user response and generating a confusion error matrix based upon the recorded user responses;

analyzing the confusion error matrix to determine the user's ability to accurately perceive each distinctive feature correlated with a test word or syllable presented; and associating distinctive features of the portions of test audio with operational parameters of the communication channel.

10. The method of claim 9, further comprising adjusting at least one of the operational parameters of the communication channel according to said analyzing step.

11. The method of claim 10, wherein the communication channel comprises an acoustic environment formed by an architectural structure.

12. The method of claim 10, wherein the communication channel comprises an underwater acoustic environment.

13. The method of claim 10, wherein the communication channel comprises an aviation environment affecting speech and hearing.

14. The method of claim 13, wherein the effects include at least one of G-force, masks, and the Lombard effect.

15. The method of claim 10, wherein the portions of test audio comprise speech from a speaker experiencing at least one of stress, fatigue, and deception.

16. A system for tuning a digital hearing device comprising:

means for playing portions of test audio, wherein each portion of test audio comprises a test word or syllable that is correlated with one or more distinctive features of speech;

means for receiving, in response to each of the portions of test audio when heard by a user through the digital hearing device, a corresponding user response prior to a subsequent portion of test audio being played;

means for recording each user response and generating a confusion error matrix based upon the recorded user responses;

means for analyzing the confusion error matrix to determine the user's ability to accurately perceive distinctive features correlated with a test word or syllable presented; and means for adjusting at least one operational parameter of the digital hearing device according to said means for analyzing, wherein the at least one operational parameter is associated with the one or more distinctive features of speech.

17. The system of claim 16, further comprising means for associating distinctive features of the portions of test audio with the operational parameter of the digital hearing device, wherein said means for associating is operable prior to said means for adjusting.

18. A system for evaluating a communication channel comprising:

means for playing, over the communication channel, portions of test audio, wherein each portion of test audio comprises a test word or syllable that is correlated with one or more distinctive features of speech;

means for receiving, in response to each of the portions of test audio when heard by a user through the digital hearing device, a corresponding user response prior to a subsequent portion of test audio being played;

means for recording each user response and generating a confusion error matrix based upon the recorded user responses;

means for analyzing the confusion error matrix to determine the user's ability to accurately perceive distinctive features correlated with a test word or syllable presented; and means for associating distinctive features of the portions of test audio with operational parameters of the communication channel.

19. The system of claim 18, further comprising means for adjusting at least one of the operational parameters of the communication channel according to results obtained from said means for analyzing.

20. A machine readable storage, having stored thereon a computer program having a plurality of code sections executable by a machine for causing the machine to perform the steps of:

playing portions of test audio, wherein each portion of test audio comprises a test word or syllable that is correlated with one or more distinctive features of speech;

for each of the portions of test audio when heard by a user through a digital hearing device, receiving a corresponding user response prior to a subsequent portion of test audio being played;

recording each user response and generating a confusion error matrix based upon the recorded user responses;

analyzing the confusion error matrix to determine the user's ability to accurately perceive distinctive features correlated with a test word or syllable presented; and adjusting at least one operational parameter of the digital hearing device according to said analyzing step, wherein the at least one operational parameter is associated with the one or more distinctive features of speech.

21. The machine readable storage of claim 20, further comprising, prior to said adjusting step, associating the one or more distinctive features of the portions of test audio with the operational parameter of the digital hearing device.

22. The machine readable storage of claim 20, wherein each distinctive feature of speech is associated with at least one particular frequency characteristic and the operational parameter controls processing of frequency characteristics associated with at least one of the distinctive features.

23. The machine readable storage of claim 20, wherein each distinctive feature of speech is associated with at least one particular temporal characteristic and the operational parameter controls processing of temporal characteristics associated with at least one of the distinctive features.

24. The machine readable storage of claim 20, further comprising determining that at least a portion of the digital hearing device is sub-optimally configured for a particular user based upon said analyzing step.

25. The machine readable storage of claim 20, further comprising performing each said step of claim 18 for at least one different language.

26. The machine readable storage of claim 20, further comprising performing each said step of claim 19 for a plurality of different users of similar hearing devices.

27. A machine readable storage, having stored thereon a computer program having a plurality of code sections executable by a machine for causing the machine to perform the steps of:

playing, over a communication channel, portions of test audio, wherein each portion of test audio comprises a test word or syllable that is correlated with one or more distinctive features of speech;

recording each user response and generating a confusion error matrix based upon the recorded user responses analyzing the confusion error matrix to determine the user's ability to accurately perceive distinctive features correlated with a test word or syllable presented; and associating distinctive features of the portions of test audio with operational parameters of the communication channel.

28. The machine readable storage of claim 27, further comprising adjusting at least one of the operational parameters of the communication channel according to said analyzing step.

29. The machine readable storage of claim 28, wherein the communication channel comprises an acoustic environment formed by an architectural structure.

30. The machine readable storage of claim 28, wherein the communication channel comprises an underwater acoustic environment.

31. The machine readable storage of claim 28, wherein the communication channel comprises an aviation environment affecting speech and hearing.

32. The machine readable storage of claim 31, wherein the effects include at least one of G-force, masks, and the Lombard effect.

33. The machine readable storage of claim 28, wherein the portions of test audio comprise speech from a speaker experiencing at least one of stress, fatigue, and deception.

* * * * *